(12) United States Patent
Halpern et al.

(10) Patent No.: US 9,539,374 B2
(45) Date of Patent: Jan. 10, 2017

(54) DONATED BLOOD COLLECTION KIT

(75) Inventors: Lise N. Halpern, Amherst, MA (US);
Tim Costello, Marshfield, MA (US);
Jonathan White, Stonington, CT (US)

(73) Assignee: Haemonetics Corporation, Braintree, MA (US)

( * ) Notice: Subject to any disclaimer, the term of this patent is extended or adjusted under 35 U.S.C. 154(b) by 722 days.

(21) Appl. No.: 12/778,710

(22) Filed: May 12, 2010

(65) Prior Publication Data
US 2011/0281346 A1 Nov. 17, 2011

(51) Int. Cl.
*C12M 1/00* (2006.01)
*B65B 5/00* (2006.01)
(Continued)

(52) U.S. Cl.
CPC ............ *A61M 1/02* (2013.01); *B01L 3/5453* (2013.01); *B01L 9/54* (2013.01);
(Continued)

(58) Field of Classification Search
CPC .............. C12M 1/00; B65B 5/00; A61M 1/02; A61M 2205/6054; A61M 2205/6063; A61M 2205/6072; A61M 2209/06; B01L 3/5453; B01L 9/54
(Continued)

(56) References Cited

U.S. PATENT DOCUMENTS 3,228,395 A   1/1966   Gewecke ..................... 128/214
4,893,636 A   1/1990   Cook et al. ................... 128/764
(Continued)

FOREIGN PATENT DOCUMENTS

EP   0 832 689 A2   4/1998   ............... B01L 3/00
JP   2002-527148   8/2002   ............. A61M 1/02
(Continued)

OTHER PUBLICATIONS

International Searching Authority, International Search Report—International Application No. PCT/US2011/034150, dated Aug. 18, 2011, together with the Written Opinion of the International Searching Authority, 11 pages.
(Continued)

*Primary Examiner* — Andrew Perreault
(74) *Attorney, Agent, or Firm* — Sunstein Kann Murphy & Timbers LLP (57) ABSTRACT

A donated blood collection kit includes an easy-to-open closed container. Stored within the container are items necessary or useful for collecting donated blood, such as an antiseptic scrub, an antiseptic swab, test tubes, a blood collection container, a gauze pad and a sheet of pre-printed adhesive barcode labels. Each kit is assigned a unique identification when the kit is manufactured. The identification may eventually be used as the unique donor identification for a unit of donated blood that is collected using the items in the kit. The container is pre-labeled with the unique identification, such as by a barcode or an RF-ID tag. The test tubes and, if included, the blood collection container are pre-labeled with the same unique donor identification. The adhesive barcode labels in the container are pre-printed with the same unique donor identification and may be affixed to items that are not provided in the kit but, nonetheless, should be associated with the unit of blood that may be collected using the kit. Information about lot numbers and expiration dates for the items in the kit may be encoded in the kit's unique identification and/or stored in a database in association with the kit's identification.

18 Claims, 4 Drawing Sheets

(51) Int. Cl.
*A61M 1/02* (2006.01)
*B01L 3/00* (2006.01)
*B01L 9/00* (2006.01)

(52) U.S. Cl.
CPC ............ *A61M 2205/6054* (2013.01); *A61M 2205/6063* (2013.01); *A61M 2205/6072* (2013.01); *A61M 2209/06* (2013.01)

(58) Field of Classification Search
USPC .... 206/570, 569, 571, 459.5; 435/6.11, 6.12
See application file for complete search history.

(56) References Cited

U.S. PATENT DOCUMENTS

| | | | |
|---|---|---|---|
| 5,190,049 A | 3/1993 | Briggs et al. | 128/760 |
| 5,194,722 A | 3/1993 | Mergenthaler et al. | 235/463 |
| 5,374,813 A | 12/1994 | Shipp | 235/375 |
| 5,640,000 A | 6/1997 | Spriet et al. | 235/375 |
| 5,671,362 A | 9/1997 | Cowe et al. | 395/228 |
| 5,848,593 A | 12/1998 | McGrady et al. | 128/897 |
| 5,935,775 A | 8/1999 | Savjani | 435/4 |
| 6,102,871 A | 8/2000 | Coe | 600/575 |
| 6,176,836 B1* | 1/2001 | Trudil et al. | 206/569 |
| 6,605,223 B2 | 8/2003 | Jorgensen et al. | 210/745 |
| 6,730,071 B1 | 5/2004 | Dassa | 604/408 |
| 6,780,645 B2 | 8/2004 | Hayter et al. | 436/8 |
| 7,147,626 B2 | 12/2006 | Goodman et al. | 604/317 |
| 7,354,190 B2 | 4/2008 | Demers et al. | 366/142 |
| 7,461,968 B2 | 12/2008 | Demers et al. | 366/152.1 |
| 7,632,078 B2 | 12/2009 | Demers et al. | 417/477.2 |
| 7,632,080 B2 | 12/2009 | Tracey et al. | 417/477.9 |
| 2003/0004751 A1 | 1/2003 | Ng et al. | 705/2 |
| 2003/0018289 A1 | 1/2003 | Ng et al. | 604/6.01 |
| 2004/0044326 A1 | 3/2004 | Kranz et al. | 604/408 |
| 2005/0095141 A1 | 5/2005 | Lanigan et al. | 417/53 |
| 2005/0095152 A1 | 5/2005 | Dale | 417/477.2 |
| 2005/0095576 A1 | 5/2005 | Demers et al. | 435/4 |
| 2005/0096583 A1 | 5/2005 | Demers et al. | 604/15 |
| 2006/0196951 A1 | 9/2006 | Lowmaster | 235/494 |
| 2007/0219480 A1 | 9/2007 | Kamen et al. | 604/20 |
| 2007/0219496 A1 | 9/2007 | Kamen et al. | 604/131 |
| 2007/0219597 A1 | 9/2007 | Kamen et al. | 607/60 |
| 2007/0228071 A1 | 10/2007 | Kamen et al. | 222/52 |
| 2007/0253463 A1 | 11/2007 | Perry et al. | 374/208 |
| 2008/0058697 A1 | 3/2008 | Kamen et al. | 604/6.13 |
| 2008/0175719 A1 | 7/2008 | Tracey et al. | 417/38 |
| 2009/0209933 A1 | 8/2009 | Zylberberg et al. | 604/408 |
| 2009/0291449 A1* | 11/2009 | Knapp et al. | 206/569 |

FOREIGN PATENT DOCUMENTS

| | | | | |
|---|---|---|---|---|
| JP | 2010-66833 | | 3/2010 | ............ G07G 1/06 |
| WO | WO 00/21590 | | 4/2000 | ............ A61M 1/36 |
| WO | WO 2009/143339 | | 11/2009 | ............ G06K 9/00 |
| WO | WO 2009/143339 A1 | | 11/2009 | ............ G06K 9/00 |

OTHER PUBLICATIONS

Hohberger, Clive P., "ISBT 128: The New Bar Code Symbology for World Blood Products Labeling," *ISBT 128 Bar Code Symbology*; [online] Apr. 23, 1999 Retrieved from: http://www.sanguis.ru/sanguis/otdel/asu/128sym.htm.

Butch, Suzanne, et al., "ISBT 128 An Introduction 128" 3rd Edition, ICCBBA, Inc., 2006.

Bar Code 101, [online] Mar. 14, 2006; 10 pages Retrieved from: http://web.archive.org/web/20060314054404/http://www.barcodepower.com/barcode 101 . . . .

Digi-Trax Corporation, image of label [online] Oct. 4, 2007 Retrieved from http://www.digi-trax.com/isbt44c.jpg.

International Searching Authority, Internationals Search Report and Written Opinion pertaining to International Application No. PTC/US2011/034150, dated Aug. 29, 2011, 11 pages.

Japanese Patent and Trademark Office, Office Action—Application No. 2013-510,121, 3 pages, dated Feb. 24, 2015.

Japanese Patent and Trademark Office, Office Action—Application No. 2013-510,121, 2 pages, dated Feb. 24, 2015 (English).

* cited by examiner

DONATED BLOOD COLLECTION KIT

TECHNICAL FIELD

The present invention relates to donated blood collection equipment and, more particularly, to kits of parts utilized in the collection of donated blood.

BACKGROUND ART

Human blood and blood components, such as blood plasma, are critically important to every modern health care system. Blood or one or more of its components is used to care for patients who suffered blood loss due to accidents, surgery and the like, or who have certain diseases. Most blood and blood components are obtained from human volunteer donors. For example, the American Red Cross organization operates blood drives in the United States to solicit donors and collect donated blood.

Collecting donated blood is a labor-intensive highly controlled process to assure the safety of the blood product and of the volunteer donor. Collection of blood, and the conversion of that blood into blood component products for transfusion, is controlled and regulated at the same level of rigor as pharmaceutical manufacturing practices. All components, staff and actions involved in the process must be carefully documented. All lot numbers and expiration dates of products used in the process must be tracked and associated with the specific blood donation. These products include a sterile, single-use blood collection container and a variety of other products. Potential donors are questioned about their health and lifestyle, their vital signs are taken and their basic health is checked. Donors cleared to donate have their arms carefully scrubbed with a series of specific skin cleaning products.

A portion of each unit of donated blood will be tested to identify the blood's type and to screen out blood that may be contaminated with diseases or impurities. To facilitate such testing, once a needle has been inserted into a donor's vein, blood samples are drawn and introduced into one or more small sealed evacuated test tubes. After the needle is withdrawn, a gauze pad and a bandage are typically applied to the needle stick location.

Thus, multiple items are required to collect a unit of blood. The items used in a single donation might include a blood collection container, a donor information sheet, multiple arm scrubs, gauze pads, tape, one or more test tubes, a disposable sample site, and a bandage. These items are typically purchased from a variety of different suppliers and stocked in boxes or other containers stored in various locations scattered about a blood donation center. Blood collection technicians must gather these items during the blood donation process.

Items, such as blood collection containers and arm wipes, are manufactured in lots. Each manufactured lot of each item has an expiration date. Blood donation technicians must be careful not to use items whose lots have expired, because blood collected using an expired item may be deemed unsuitable and would be discarded. Furthermore, if a lot of items is later suspected or found to be defective, such as due to contamination or a manufacturing error, all blood collected using any item from the identified lot must be discarded.

Blood is considered to be a manufactured medical product, in that each unit of blood must be traceable back to its donor, as well as to the equipment that was used to collect and process the blood. Thus, blood donation centers must keep records that associate each unit of collected blood with its donor, as well as with the lot numbers of all the items used to collect the blood. This information may then be provided to hospitals or other organizations that use the blood, or it may be used in a quality assurance process for the blood product.

To associate a unit of blood with a donor, a blood donation technician typically uses sheets of adhesive labels having barcodes preprinted on them. A sheet typically contains several identical barcode labels, the format of which is prescribed by regulation. After gathering the necessary items, but prior to collecting blood from a donor, the technician peels the labels off the sheet and applies one such label to the donor's information sheet, another label to each test tube and a label to the blood collection container. However, keeping track of the lot numbers of "consumable" items, such as blood collection containers, disinfecting wipes and bandages, and correlating these lot numbers and their respective expiration dates with units of blood requires manual data entry which, of course, takes time and is susceptible to human error.

SUMMARY OF EMBODIMENTS

An embodiment of the present invention provides a kit for facilitating collecting donated blood. Each kit includes at least one sealed test tube and at least two adhesive labels inside a closed container. Each kit has a unique identification, and each kit has a computer-readable representation (such as a barcode or an RF-ID tag) of data that includes the unique identification of the kit. The test tube(s) and the adhesive labels also have computer-readable representations of data that include the unique identification of the kit. Thus, components of the kit are associated with the kit via the kit's identification. The test tube(s) may be used to store one or more blood samples. The adhesive labels are releasably attached to a release sheet substrate. The adhesive labels may be removed from the release sheet substrate and attached to other items, such as a donor information sheet or a blood collection bag, that are used to collect the donated blood.

Optionally, each test tube may have an expiration date, and the unique identification of the kit may be associated, in a computerized database, with the expiration date of the test tube or, if there is more than one test tube, with the earliest expiration date of the test tubes.

The kit may include one or more blood collection containers within the closed container. Each blood collection containers may include one or more blood bags, one or more blood collection sets, one or more containers configured for use with an automated whole blood collector and/or one or more containers configured for use with an apheresis system.

Each such blood collection container may have a computer-readable representation (such as a barcode or an RF-ID tag) of data including the unique identification of the kit. Each blood collection container may have an expiration date. As noted, each test tube may also have an expiration date. The unique identification of the kit may be associated, in a computerized database, with the earliest expiration date of the blood collection container(s) and the test tubes. Thus, the unique identification of the kit may be associated with the date on which the earliest expiring item of the kit expires.

Optionally, the kit may include material, such as an antiseptic wipe and an arm scrubbing device, suitable for preparing a venipuncture site for a needle stick disposed within the closed container. The kit may include material, such as gauze and a bandage, suitable for treating a wound after a needle stick at a venipuncture site disposed within the closed container. The material suitable for preparing the venipuncture site and the material suitable for treating the wound after the needle stick may have respective expiration dates. The unique identification of the kit may be associated, in a computerized database, with the earliest expiration date of the material suitable for preparing the venipuncture site and the material suitable for treating the wound after the needle stick and, optionally, the blood collection container (s) (if present) and the test tube(s). Thus, the unique identification of the kit may be associated with the date on which the earliest expiring item of the kit expires.

The kit may include a blood donor information sheet disposed within the closed container. The blood donor information sheet may have a computer-readable representation, such as a barcode or an RF-ID tag, of data including the unique identification of the kit.

The computer-readable representation of data that includes the unique identification of the kit may include an optically computer-readable representation of data, such as a barcode or a concatenated barcode. The computer-readable representation of data that includes the unique identification of the kit may conform to the International Society of Blood Transfusion system for identifying, labeling and processing human blood known as ISBT 128. As noted, the computer-readable representation of data that includes the unique identification of the kit may include an RF-ID tag.

An embodiment of the present invention provides a method for providing a kit for collecting donated blood. A kit container is provided. The kit container has a computer-readable representation, such as a barcode or an RF-ID tag, of data including a unique identification of the kit. At least one test tube and at least two adhesive labels are disposed in the kit container. The adhesive labels are releasably attached to a release sheet substrate. Each test tube and each adhesive label has a computer-readable representation of data including the unique identification of the kit. After the test tube(s) and the release sheet substrate have been disposed in the kit container, the kit container is closed.

Each test tube may have an expiration date, and the unique identification of the kit may be associated, in a computerized database, with the earliest expiration date of the test tube having the earliest expiration date.

Optionally, before closing the kit container, one or more blood collection containers may be disposed in the kit container. Each such blood collection container may have a computer-readable representation of data including the unique identification of the kit. Each such blood collection container may have an expiration date, and the unique identification of the kit may be associated, in a computerized database, with the expiration date of the test tube or blood collection container having the earliest expiration date. Thus, the unique identification of the kit may be associated with the date on which the earliest expiring item of the kit expires.

Material suitable for preparing a venipuncture site for a needle stick and material suitable for treating a wound after a needle stick at a venipuncture site may be disposed in the kit container, before closing the kit container. The Material suitable for preparing a venipuncture site for a needle stick and the material suitable for treating a wound after a needle stick may have respective expiration dates. The unique identification of the kit may be associated, in a computerized database, with the earliest expiring item.

Donated blood may be collected in the blood collection container, and the donated blood may be associated, in a computer database, with the unique identification of the kit.

A concatenated barcode may be formed, such as a concatenated barcode that includes the unique identification of the kit and a computer-readable representation of data including an expiration date of the donated blood.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Definitions: As used in this description and in the accompanying claims, the following terms shall have the meanings indicated, unless the context otherwise requires:

Blood collection container—a vessel used to store collected blood.

Blood collection set or automated blood collection set—a blood collection container configured for use in conjunction with a specific blood collection device or system, such as an apheresis system or an automated whole blood collection (AWBC) system. Examples of such systems include the Cymbal system for automated red cell collection and the MCS apheresis system, both available from Haemonetics Corp., 400 Wood Rd., Braintree, Mass., 02184.

Blood bag—a blood collection container configured for use without a specific blood collection device.

Venipuncture site—a location on the surface of a body of a blood donor where a needle may be, or was, inserted to obtain venous blood.

In accordance with embodiments of the present invention, methods and apparatus are disclosed for providing kits of items necessary or useful for collecting donated blood. Each kit bears a unique identification, which may eventually be used as the unique donor identification for a unit of donated blood that is collected using the items in the kit. Each kit is assigned its unique identification when the kit is manufactured. One or more of the items in the kit may be pre-labeled with the same unique identification.

The kit includes pre-printed adhesive labels bearing the kit's unique identification. These labels may be applied to other items, such as donor information sheets, that may not be provided in the kit, but that may, nonetheless, be used in relation to collecting the blood.

Furthermore, information about lot numbers and expiration dates for the items in the kit may be encoded in the kit's unique identification and/or stored in a database in association with the kit's identification. Thus, the kit provides a blood collection technician with most or all of the items he/she needs to collect a unit of blood. In addition, most or all of the items associated with the collected blood are pre-associated with the unique identification, relieving the technician from manually entering information and reducing the possibility of human error.

Figure 1:
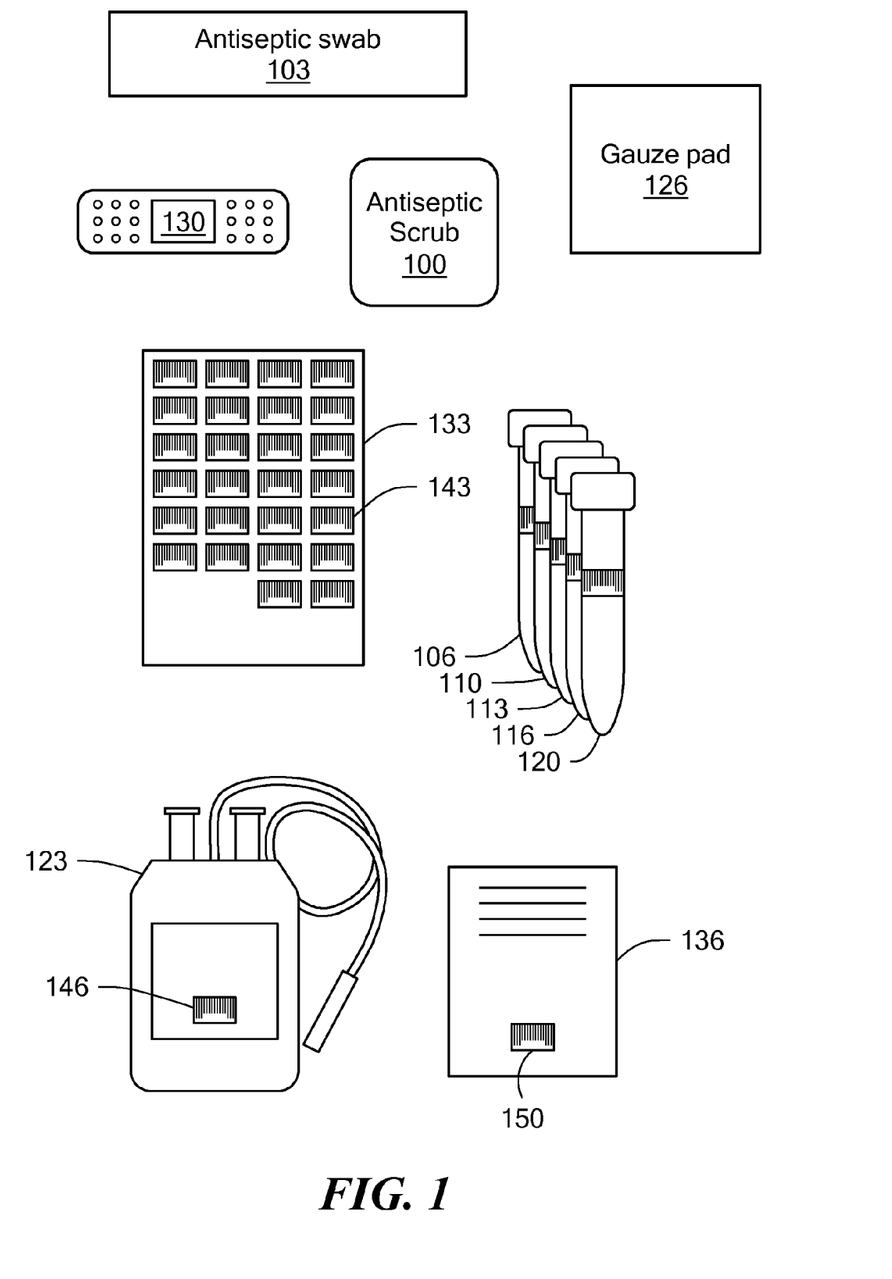
FIG. 1 is a schematic diagram illustrating items in a donated blood collection kit, according to an embodiment of the present invention.

The contents of one embodiment of such a kit are illustrated in FIG. 1. The kit contents include an antiseptic scrub 100, an antiseptic swab 103, several pre-labeled sealed evacuated test tubes 106, 110, 113, 116 and 120, a pre-labeled blood collection container 123, a gauze pad 126, a bandage 130, a sheet 133 of a small number of pre-printed adhesive barcode labels and a pre-labeled donor information sheet 136. (As used herein, the term "barcode" includes 1D (one-dimensional) and 2D (two-dimensional) optically or otherwise machine readable representations of data, regardless of the symbols, shapes, colors or geometries used.) The test tubes 106-120, the blood collection container 123 and the donor information sheet 136 are pre-labeled with the kit's unique identification. This labeling may be accomplished by encoding the unique identification of the kit in a computer-readable representation of data, such as a barcode or an RF-ID tag, printed on or affixed to the respective item. Exemplary barcodes 140, 143, 146 and 150 are shown in FIG. 1.

Figures 2, 3:
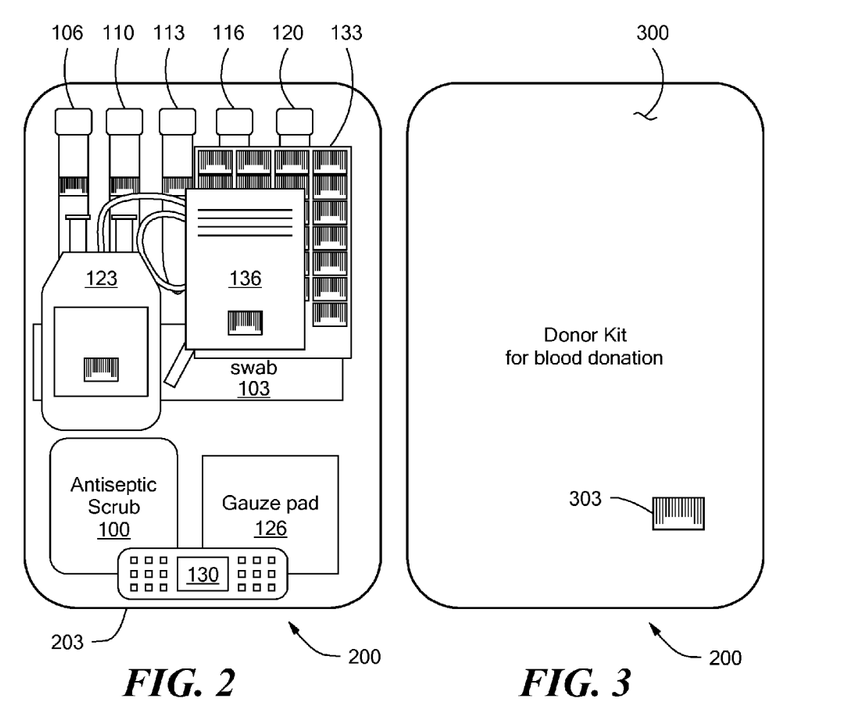
FIG. 2 is a top schematic diagram of a donated blood collection kit, with a top cover removed for clarity, according to an embodiment of the present invention.
FIGS. 3 and 4 are top and side schematic diagrams, respectively, of the donated blood collection kit of FIG. 2.

FIG. 2 is a top view of a kit 200 with its cover removed or opened for clarity. The kit 200 includes a tray or other suitable housing 203, in which the remaining items 100-136 are disposed. The housing 203 may include compartments, dividers or other structures (not shown) to keep the items 100-136 organized and to prevent shifting of the items 100-136 during shipment and handling. The housing 203 may be may be made of any suitable material, such as plastic, paper, paperboard or cardboard, and the housing 203 may be manufactured using any suitable technique, such as vacuum molding.

Figure 4:
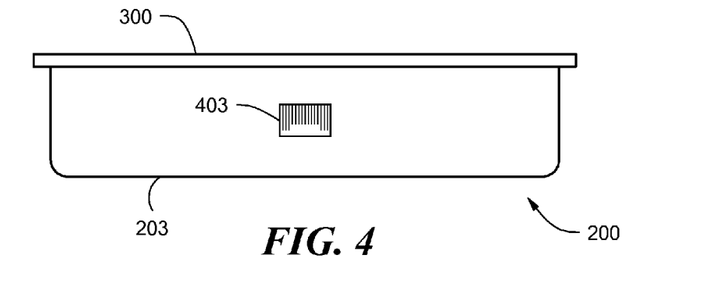

FIGS. 3 and 4 are top and side views, respectively, of the kit 200 with a cover 300 in place. The cover 300 may be made of any suitable material, such as plastic, paperboard, cardboard or paper. The cover 300 may be attached to the housing 203 by any suitable technique or material, such as an adhesive, ultrasonic welding or heat welding, that enables a technician to relatively easily open or remove the cover 300. However, while the cover is attached to the housing 203, the housing 203 and the attached cover 300 collectively protect the items 100-136 disposed within the kit. In some embodiments, the housing 203 and the attached cover 300 provide a hermetically sealed container. In another embodiment (not shown), the cover may be provided by flaps (not shown) that extend from the housing 203 and may be folded, so as to close the kit. The flaps may then be held in place by an adhesive, elastic or other strap, or the flaps may be folded over each other so as to hold them closed. Such an embodiment may be made from paperboard, for example. As used herein, as used with respect to the housing and its cover, the term "sealed" means closed. Packaging may also include specialized foil wrapping necessary to appropriately store and protect the blood collection container 123. The total amount of disposable packaging material may be less than in the prior art, where the items are individually wrapped.

One or more barcodes or RF-ID tags, exemplified by barcodes 303 and 403, may be affixed to, or printed on, the housing 203 and/or the cover 300. These barcodes or RF-ID tags encode the unique identification of the kit. Placing a barcode 403 on the side of the housing 203 enables users to scan the barcode 403, even if several kits are stacked and the barcodes 303 on the covers 300 are obscured.

Figure 5:
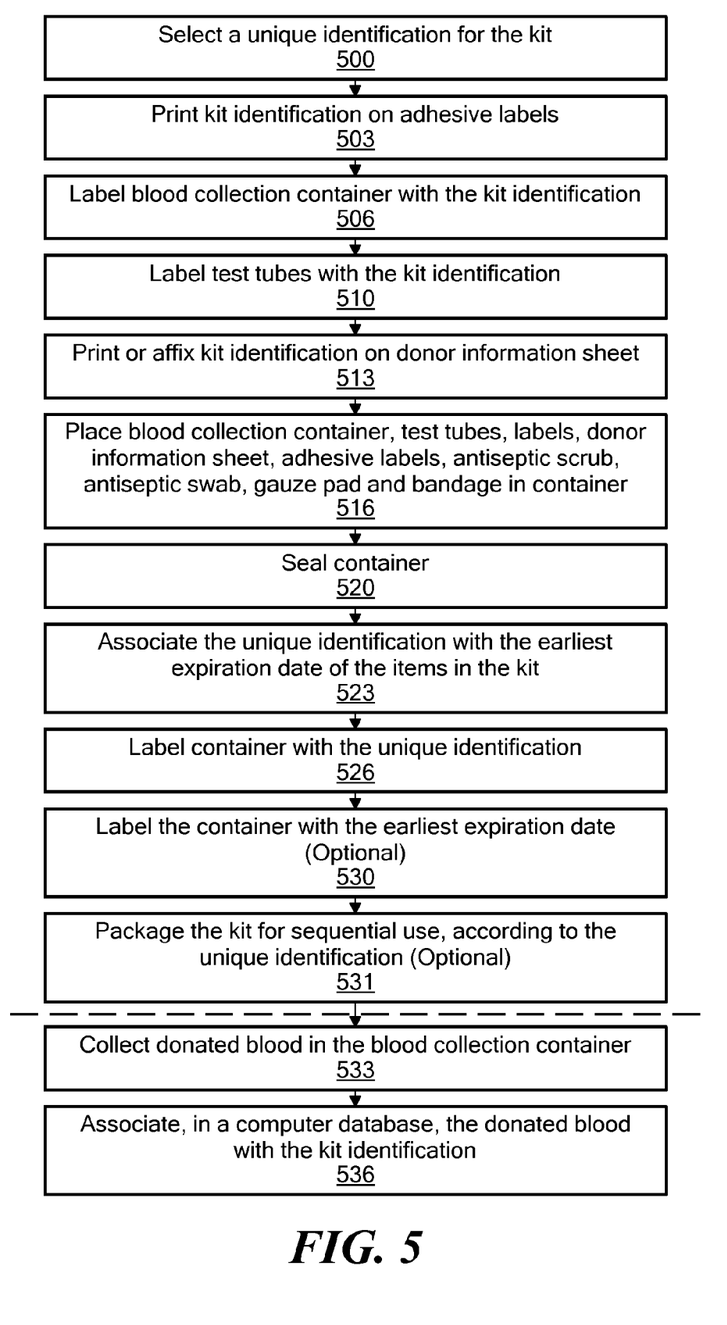
FIG. 5 is a flowchart illustrating operations performed in manufacturing and using a donated blood collection kit, according to embodiments of the present invention.

As noted, each kit is assigned its unique identification when the kit is manufactured. FIG. 5 is a flowchart illustrating operations performed in manufacturing and using a kit. At 500, a unique identification for a given kit is selected. The identification preferably conforms to the International Society of Blood Transfusion system for identifying, labeling and processing human blood known as ISBT 128 or another blood labeling standard. According to ISBT 128, a unique donation identification includes a 13-character identifier built up from three elements: an identification of a collection facility, an identification of the year in which the donation was (or is to be) collected, and a sequence number assigned by the collection facility for the donation. Thus, the kit identification may be specific to the facility, such as a branch of the American Red Cross, which will use the kit to collect blood.

An operator or automated manufacturing system (not shown) may enter or select the facility identifier, for example based on the identity of the customer that ordered the kit. The sequence number may be sequentially generated beginning at 1 (if this is the first order for this customer) or at one more than the last identification used in the most recently filled order for the same customer. Optionally, the customer may specify a beginning sequence number for an order of kits.

Similarly, an operator or an automated manufacturing system may enter or specify the year identifier. Optionally, the customer may specify the year in an order, such as if the customer anticipates using the ordered kits in a subsequent calendar year.

At 503, a sheet of adhesive labels is printed, such that each label bears the kit's identification. The labels may be adhered to a suitable release sheet substrate, as is well known. The labels may be printed by a thermal transfer printer, a laser printer, an ink-jet printer or any other suitable printer.

At 506, any included blood collection container, such as a blood bag, is labeled with the kit's identification, generally by affixing an automatically generated adhesive label, bearing an appropriate barcode onto the container. One or more of the adhesive labels printed at 503 may be attached to the blood collection container. Alternatively, an RF-ID tag may be attached to the container. The RF-ID tag may be programmed with the kit's identification before or after it is attached.

At 510, each test tube that is to be included in the kit is labeled with the kit identification. The test tubes may be labeled in a manner similar to that used to label the blood collection container. Any number of test tubes may be included in each kit, such as according to a customer's specifications, customary industry practices (i.e., the number of test tubes necessary to carry out standard blood tests), etc.

At 513, the kit's identification is added to a donor information sheet, if such a sheet is included in the kit. In some cases, the donor information sheet is custom printed for each kit, in which case the kit identification may be printed at the same time the rest of the donor information sheet is printed. In some other cases, the kit's identification may be printed a generic pre-printed donor information sheet, or an adhesive label bearing the kit's identification (such as one of the labels produced at 503) may be automatically or manually attached to the generic pre-printed donor information sheet.

Items making up the contents of the kit, such as the labeled blood collection container, the labeled test tubes, the labeled donor information sheet, the adhesive labels, an antiseptic scrub, an antiseptic swab, a gauze pad and a bandage, are placed into a container at 516, and the container is closed at 520. The kit may be assembled automatically, manually or using a combination of automatic and manual procedures. It should be noted that some embodiments of the kit contain different combinations of contents. For example, some embodiments do not contain any blood collection containers.

Each of the items, with the possible exceptions of the donor information sheet and the adhesive labels, typically has a manufacture lot number and an expiration date. At 523, the earliest of the expiration dates for the items placed in the kit is associated with the kit's identification, such as by storing this information in a computer database. Once the earliest expiring item in a kit expires, the entire kit is deemed to have expired. Expired kits may be disposed of or, alternatively, broken down and unexpired items may be used to make up new kits.

Lot numbers for items in inventory, and the expiration dates associated with these lot numbers, may be stored in an automated inventory system. For example, this information may be provided by the manufacturers of the respective items when the items are ordered or shipped to the enterprise that produces the blood collection kits. These lot numbers and expiration dates may be copied to, or associated with, database records that represent manufactured kits. Information about the kits, the lot numbers and expiration dates may be stored in a kit manufacturer's server computer.

At 526, the container is labeled with the kit's unique identification. As noted, the kit may be labeled by applying or printing a barcode or an RF-ID tag on the kit, such as on the cover and/or side of the container.

Optionally, at 530, the kit may be labeled with the earliest expiration date determined at 523. The earliest expiration date may be printed in an eye (i.e., human) readable form on the cover and/or side of the container. Optionally or alternatively, the earliest expiration date may be encoded and included in the barcode or RF-ID tag that encodes the kit's unique identification. (In this case, operations 530 and 526 may be combined.) For example, ISBT 128 specifies that an expiration date/time is to appear in the lower-right 2-inch by 2-inch quadrant of a label. (According to ISBT 128, the lower-right quadrant also includes a barcode that encodes special testing.) Thus, the earliest expiration date may be included in the lower-right quadrant of an IDBT 128-compliant label applied to, or printed on, the kit. Later, after blood has been collected with the kit, a different expiration date based on the useful shelf life of the blood may be associated with the blood collection container, and an adhesive label bearing a computer-readable encoding of the new expiration date may be applied over the kit's expiration date.

Optionally or alternatively, any combination of information about the kit, its contents and/or one or more expiration dates may be encoded in a concatenated barcode. For example, a concatenated barcode may include lot numbers and expiration dates of several or all of the components of a kit, as well as the kit's unique identification. In another example, after blood has been collected using a kit, a barcode that encodes the blood's expiration date may be appended to a barcode previously associated with the kit, such as the kit's unique identification, and the resulting concatenated barcode may be printed on a label. The label may then be adhered to the now full blood collection container over the kit's unique identification barcode or in another location.

Optionally, kits may be packaged in dispensers or other containers that ensure or facilitate use of the kits in sequential order, according to the unique identifications of the kits. If so, at 531, the kit is packaged in such a dispenser or other container.

At a blood donation center, blood may be collected in the blood collection container of a kit, as indicated at 533. In addition, the donated blood may be associated with the kit identification, as indicated at 536.

Figure 6:
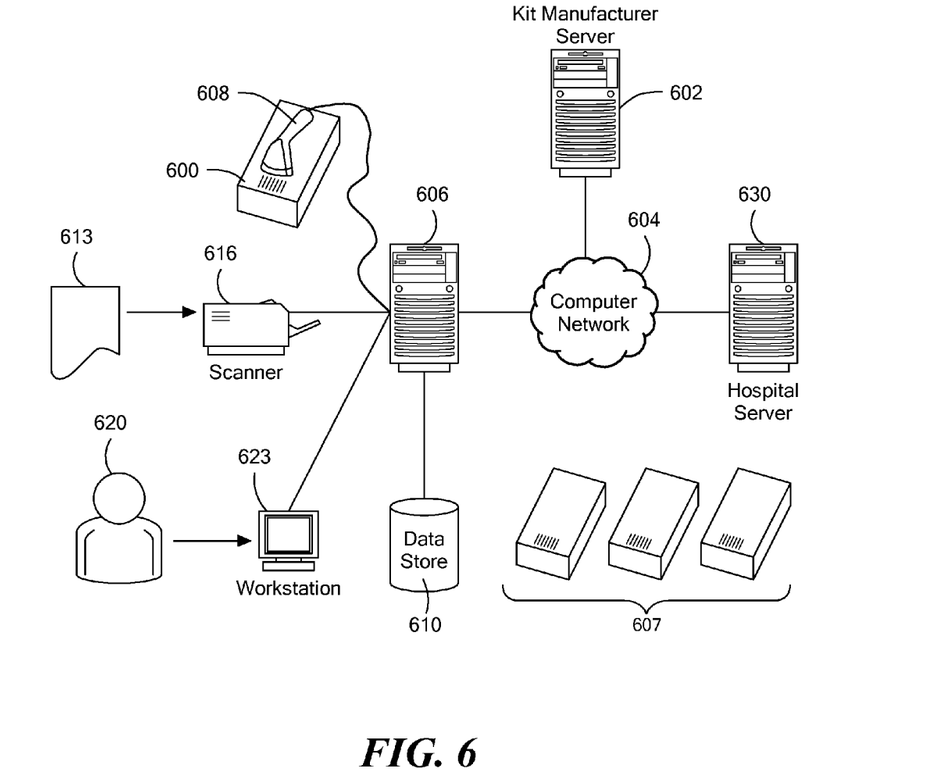
FIG. 6 is a schematic diagram illustrating how donated blood may be associated with a kit's identification and how information about the blood and the kit may be disseminated, according to embodiments of the present invention.

FIG. 6 is a schematic diagram illustrating how the donated blood may be associated with the kit's identification and how information about the blood and the kit may be disseminated. When a kit 600 is ordered or provided by the kit manufacturer to a blood collection organization, information about the kit 600, such as its unique identification, the earliest expiration date for any item in the kit 600, lot numbers for the items in the kit 600, etc., may be provided by a kit manufacturer server 602, via a computer network 604, to a server 606 operated in association with the blood collection organization. Information about a plurality of kits 607 may be stored in the server 606.

Later, when the kit 600 is used to collect donated blood, its kit identification information and expiration date may be read, such as with a portable barcode reader 608. This information may be stored by the server computer 606 in a data store 610, such as in a database. As noted, the server 606 already stores information about the kit's expiration date, etc. Thus, if the kit has expired, a warning may be provided, such as by a visible or audible indicator provided by the barcode reader 608. Furthermore, a blood collection organization or any other organization possessing the kit 600 may proactively generate a report of otherwise identify kits that have expired or are about to expire.

A blood donor information sheet 613 containing information about a person who donated, or is about to donate, blood may be scanned by a document scanner 616 coupled to the server 606, and information from the donor information sheet 613 may be stored in the data store 610 in association with the information about the kit 600. The information on the donor information sheet 613 may include the identity of, and contact information for, the donor. Recall that the kit's identification information may have been pre-printed on, or attached to, the donor information sheet 613. Thus, this identification information on the sheet 613 may be captured by the scanner 616, and this identification may be used to automatically associate the other scanned information from the sheet 613 with the information about the kit 600 that was or will be stored in the data store 610.

Optionally or alternatively, a user, such as the blood collection technician 620, may manually enter some or all of the information about the blood donor via a workstation 623 connected to the server 606. Customers using electronic donor history systems may choose to use kits without donor history sheets included.

As noted, after blood has been collected, the blood is typically tested and processes, usually by a laboratory, typically some time after the donation. After being tested and processed, the blood is banked and then made available to user organizations. When a unit of blood is selected for delivery to a user organization, such as to a hospital, information about the blood may be sent electronically by the server 606, via the computer network 604, to a server 630 operated in association with the user organization. This information may include, for example, the kit (and, therefore, the donated blood) unique identification, the earliest expiration date of any item in the kit 600 used to collect the blood, the expiration date of the blood, lot number information for all the items used to collect the blood, results from the laboratory testing (such as blood type), etc.

The user organization may use this information to manage the blood, such as to determine by when it should be used or discarded. In addition, if a problem is later discovered or suspected with any of the items used to collect the blood, the data store 610 or the hospital server 630 may be queried to identify blood units that were collected using items in suspected or known bad lots. The identified blood may then be discarded or retested, as appropriate.

Although an embodiment of a donated blood collection kit has been described as including a particular set and quantity of items, other embodiments of such a kit may include other items, such as a quantity of povidone-iodine (PVPI) topical antiseptic, an "I donated" button or other favor, a candy, small package of cookies or other snack, as well as items not listed here. Furthermore, other embodiments of such a kit may include other combinations or quantities of these and other items. In addition, some items may be omitted from some embodiments. However, items that have expiration dates or lot numbers are preferably treated as described above, with reference to blood collection containers, test tubes, etc.

Some embodiments of a donated blood collection kit include blood bags to store donated blood. However, some other embodiments may include one or more components, such as one or more blood collection sets, used with an existing or future automated blood collection or apheresis systems or another system, such as an automated whole blood collector (AWBC). A suitable AWBC is described in U.S. Pat. No. 6,113,554, titled "Automatic Whole Blood Collection System," by Ronald O. Gilcher, et al., and assigned to the assignee of the present application, the entire contents of which are hereby incorporated by reference herein. The kit may be used with any blood collection data management system.

In accordance with exemplary embodiments, donated blood collection kits and associated methods have been described. While the invention is described through the above-described exemplary embodiments, it will be understood by those of ordinary skill in the art that modifications to, and variations of, the illustrated embodiments may be made without departing from the inventive concepts disclosed herein. For example, although some aspects of manufacturing and using such kits have been described with reference to a flowchart, those skilled in the art should readily appreciate that functions, operations, decisions, etc. of all or a portion of each block, or a combination of blocks, of the flowchart may be combined, separated into separate operations or performed in other orders. Furthermore, disclosed aspects, or portions of these aspects, may be combined in ways not listed above. Accordingly, the invention should not be viewed as being limited to the disclosed embodiments.

What is claimed is:

1. A system for facilitating collecting donated blood, the system comprising:
    a plurality of kits, each kit comprising a closed container having a computer-readable representation of data including a unique identification of the kit, the container having disposed therewithin:
        at least one sealed test tube, devoid of any blood product, having a computer-readable representation of data including the unique identification of the kit and an expiration date of the test tube; and
        a release sheet substrate having a plurality of adhesive labels releasably attached thereto, each of the plurality of adhesive labels having a computer-readable representation of data including the unique identification of the kit; and
    a computerized database storing, for each kit:
        the unique identification of the kit; and
        information that associates the unique identification of the kit with the expiration date of the test tube in the kit having the earliest expiration date.

2. A system according to claim 1, further comprising at least one blood collection container having a computer-readable representation of data including the unique identification of the kit disposed within each closed container.

3. A system according to claim 1, further comprising material suitable for preparing a venipuncture site for a needle stick disposed within each closed container.

4. A system according to claim 3, wherein the material comprises an antiseptic wipe and an arm scrubbing device.

5. A system according to claim 1, further comprising material suitable for treating a wound after a needle stick at a venipuncture site disposed within each closed container.

6. A system according to claim 5, wherein the material comprises gauze and a bandage.

7. A system according to claim 1, further comprising a blood donor information sheet disposed within each closed container, the blood donor information sheet having a computer-readable representation of data including the unique identification of the kit.

8. A system according to claim 1, wherein the computer-readable representation of data including the unique identification of the kit comprises an optically computer-readable representation of data.

9. A system according to claim 8, wherein the optically computer-readable representation of data comprises a barcode.

10. A system according to claim 8, wherein the optically computer-readable representation of data comprises a concatenated barcode.

11. A system according to claim 1, wherein the computer-readable representation of data including the unique identification of the kit conforms to the International Society of Blood Transfusion system for identifying, labeling and processing human blood known as ISBT 128.

12. A system according to claim 1, wherein the computer-readable representation of data including the unique identification of the kit comprises an RF-ID tag.

13. A system for facilitating collecting donated blood, the system comprising:
    a plurality of kits, each kit comprising a closed container having a computer-readable representation of data including a unique identification of the kit, the container having disposed therewithin:
        at least one sealed test tube, devoid of any blood product, having a computer-readable representation of data including the unique identification of the kit and an expiration date of the test tube;
        at least one blood collection container having a computer-readable representation of data including the unique identification of the kit and an expiration date of the blood collection container; and
        a release sheet substrate having a plurality of adhesive labels releasably attached thereto, each of the plurality of adhesive labels having a computer-readable representation of data including the unique identification of the kit; and
    a computerized database storing, for each kit:
        the unique identification of the kit; and information that associates the unique identification of the kit with the earlier of:
  the expiration date of the blood collection container having the earliest expiration date; and
  the expiration date of the tube in the kit having the earliest expiration date.

14. A system according to claim 13, wherein the at least one blood collection container comprises at least one blood bag.

15. A system according to claim 13, wherein the at least one blood collection container comprises at least one blood collection set.

16. A system according to claim 13, wherein the at least one blood collection container comprises at least one container configured for use with an automated whole blood collector.

17. A system according to claim 13, wherein the at least one blood collection container comprises at least one container configured for use with an apheresis system.

18. A system for facilitating collecting donated blood, the system comprising:
  a plurality of kits, each kit comprising a closed container having a computer-readable representation of data including a unique identification of the kit, the container having disposed therewithin:
    at least one sealed test tube, each of the at least one sealed test tube being devoid of any blood product and having a computer-readable representation of data including the unique identification of the kit and an expiration date of the test tube;
    at least one blood collection container, each of the at least one blood collection container being devoid of any blood product and having a computer-readable representation of data including the unique identification of the kit and an expiration date of the blood collection container;
    a release sheet substrate having a plurality of adhesive labels releasably attached thereto, each of the plurality of adhesive labels having a computer-readable representation of data including the unique identification of the kit;
    first material suitable for preparing a venipuncture site for a needle stick disposed within the container; and
    second material suitable for treating a wound after a needle stick at a venipuncture site disposed within the container;
    wherein: the first material and the second material have respective expiration dates; and
  a computerized database storing, for each kit:
    the unique identification of the kit; and
    the expiration date of the test tube having the earliest expiration date;
    the expiration date of the blood collection container having the earliest expiration date;
    the expiration date of the first material; and
    the expiration date of the second material.

* * * * *